United States Patent [19]

Kumar et al.

[11] Patent Number: 5,658,501

[45] Date of Patent: Aug. 19, 1997

[54] SUBSTITUTED NAPHTHOPYRANS

[75] Inventors: Anil Kumar, Pittsburgh; David B. Knowles, Apollo; Barry Van Gemert, Murrysville, all of Pa.

[73] Assignee: Transitions Optical, Inc., Pinellas Park, Fla.

[21] Appl. No.: 490,258

[22] Filed: Jun. 14, 1995

[51] Int. Cl.$^6$ .......................... C08K 5/15; C07D 311/78; C07D 405/02; G02B 5/23

[52] U.S. Cl. .......................... 252/586; 549/389; 549/331; 549/60; 549/58; 548/525; 548/454; 548/364.4; 548/311.4; 546/196; 546/164; 544/375; 544/150; 524/110; 524/109; 524/90; 524/84

[58] Field of Search .......................... 252/586; 549/389, 549/331, 60, 58; 548/454, 525, 364.4, 311.4; 546/196, 164; 544/375, 150; 524/110, 109, 90, 84

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,980,089 | 12/1990 | Heller | 252/586 |
| 4,994,208 | 2/1991 | McBain et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,384,077 | 1/1995 | Knowles | 252/71 |
| 5,405,958 | 4/1995 | Van Gemert | 544/71 |
| 5,411,679 | 5/1995 | Kumar | 252/586 |

FOREIGN PATENT DOCUMENTS

| | | |
|---|---|---|
| 7-41758 | 7/1995 | Japan. |
| 7-48363 | 7/1995 | Japan. |
| 7-48566 | 7/1995 | Japan. |
| 7-48567 | 7/1995 | Japan. |

OTHER PUBLICATIONS

*Friedel–Crafts and Related Reactions*, George A. Olah, Interscience Publishers, vol. 3 Chapter XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al., J. Chem. Soc., Perkin Trans. 1, pp. 3401–3406, 1992.

*The Chemistry of Quinonoid Compounds*, S. Patai, John Wiley & Sons, Inc. Part 2, Chapter 17 (The Addition and Substitution Chemistry of Quinone) pp. 877–1144, 1980.

"Regioselective 6–Amination and 6–Arylation of 5,8–Quinolinedione Promoted by Metal Ions", Yoshida, K., et al., Bull. Chem. Soc. Jpn., vol. 61, 1988, pp. 4335–4340.

"Reaction of 1,4–Naphthoquinone with N–methylpyrrole. Selective Synthesis of Pyrrolyated 1,4–Naphthoquinones", Yoshida, K., et al, Chemistry Express, vol. 5, No. 10, 1990, pp. 749–752.

"The Reaction of Trialkylboranes with 1,4–Naphthoquinone: A New, Convenient Synthesis of 2–Alkyl–1, 4–Naphthalenediols. Evidence for a Free–Radical Chain Mechanism", Kabalka, G., J. Organomet. Chem., 33, 1971, pp. C25–C28.

"Catalytic Asymmetric Induction in Oxidation Reactions. Synthesis of Optically Active Epoxynaphthoquinones", Pluim, H., et al, J. Org. Chem. 1980, 45, pp. 2498–2502.

"Synthesis and Properties of 6–Substituted Quinoline–5, 8–dione Colour Formers", Yoshida, K., et al, J. Chem. Soc. Perkin Trans. I, 1994, pp. 2521–2523.

"Arylation of Quinones with Arenes and Palladium Acetate", Itahara, T., J. Chem. Soc., Chem. Commun., 1981, pp. 859–860.

"Reaction of Hydroxylamines with 1,4–Quinones: A New Direct Synthesis of Aminoquinones", Bittner, S., et al, Synthesis, Sep. 1994, pp. 917–919.

"Selective Synthesis and Metallochromic Properties of Pyrrolylated Quinoline–5,8–diones", Yoshida, K., et al, J. Chem. Soc., Perkin Trans. I, 1992, pp. 2713–2715.

*Organic Synthesis*, vol. 31, John Wiley & Sons, Inc., pp. 90–93, 1951.

*Organic Synthesis*, vol. 31, John Wiley & Sons, Inc., pp. 72–77, 1951.

"Fast Fading Naphtho[1,2–b]pyran Photochromics", Research Disclosure, May 1994, pp. 267–268.

Primary Examiner—Nicky Chan
Attorney, Agent, or Firm—Frank P. Mallak; Irwin M. Stein

[57] ABSTRACT

Described are novel reversible photochromic 2H-naphtho[1, 2-b] pyran compounds, examples of which are compounds having certain substituents at the number 5 carbon atom of the naphtho-portion of the naphthopyran and at the 2-position of the pyran ring. Certain substituents may also be present at the number 6, 7, 8, 9 or 10 carbon atoms of the naphtho portion of the naphthopyran. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

20 Claims, No Drawings

SUBSTITUTED NAPHTHOPYRANS

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are, reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses a blue coloring photochromic benzo-or naphthopyran having at the position alpha to the oxygen of the pyran ring a phenyl group having a nitrogen containing substituent in the ortho or para positions.

The present invention relates to novel substituted 2H-naphtho[1,2-b]pyran compounds which have been unexpectedly found to have an acceptable fade rate in addition to a high activated intensity and a high coloration rate. In particular, the use of certain substituents at the 5-position of the naphtho-portion of the naphthopyran compound increases the fade rate without the addition of acids or bases. In addition, these compounds have certain substituents at the 2-position of the pyran ring. Certain substituents may also be present at the number 6, 7, 8, 9 or 10 carbon atoms of the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 2H-naphtho[1,2-b]pyran compounds having an acceptable fade rate, high activated intensity and a high coloration rate may be prepared. These compounds may be described as naphthopyrans having certain substituents at the 2 position of the pyran ring and at the number 5 carbon atom of the naphtho- portion of the naphthopyran ring. Certain substituents may also be present at the 6, 7, 8, 9 or 10 carbon atoms of the naphtho portion of the naphthopyran ring. These compounds may be represented by the following graphic formula:

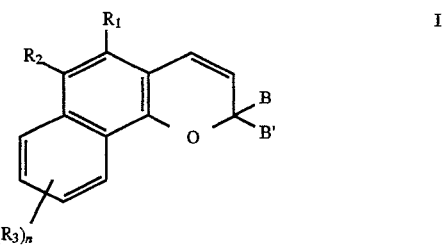

In graphic formula I, $R_1$ may be selected from the group consisting of, $-SR_7$, $-OR_4$, $-CH(COOR_7)_2$, $-CH_2COOR_7$, $-N(R_5)R_6$, $-N(R_7)C(O)R_7$, $-C(R_7)_2OH$, $-CN$, $-CF_3$, halogen, $C_1-C_6$ alkyl, $C_3-C_7$ cycloalkyl, the mono-, di- and tri- substituted aryl groups phenyl and naphthyl, unsubstituted and mono-substituted phenyl $(C_1-C_3)$ alkyl, unsubstituted and mono-substituted naphthyl $(C_1-C_3)$ alkyl, $(C_1-C_6)$ alkoxy $(C_2-C_4)$ alkyl, the unsubstituted, mono- and di-substituted heterocyclic aromatic groups pyridyl, pyrrolyl, indolyl, furanyl, e.g., furan-2-yl and furan-3-yl, benzofuranyl, e.g., benzofuran-2-yl and benzofuran-3-yl, thienyl, e.g. thien-2-yl and thien-3-yl, and benzothienyl, e.g., benzothien-2-yl and benzothien-3-yl; $R_7$ being $C_1-C_6$ alkyl, or the mono-, di- or tri-substituted aryl groups phenyl or naphthyl. $R_4$ may be hydrogen, $C_1-C_6$ alkyl, the mono- or di-substituted aryl groups phenyl or naphthyl, unsubstituted or mono-substituted phenyl or naphthyl $(C_1-C_3)$ alkyl, e.g., phenyl $(C_1-C_3)$ alkyl, mono $(C_1-C_6)$ alkyl substituted phenyl $(C_1-C_3)$ alkyl, mono $(C_1-C_6)$ alkoxy substituted phenyl $(C_1-C_3)$ alkyl, naphthyl $(C_1-C_3)$ alkyl, mono $(C_1-C_6)$ alkyl substituted naphthyl $(C_1-C_3)$ alkyl, and mono $(C_1-C_6)$ alkoxy substituted naphthyl $(C_1-C_3)$ alkyl; $C_1-C_6$ alkoxy $(C_2-C_4)$ alkyl, $C_3-C_7$ cycloalkyl, mono $(C_1-C_4)$ alkyl substituted $C_3-C_7$ cycloalkyl, $C_1-C_6$ haloalkyl, allyl, the group, $-CH(R_{14})X$, X being $-CN$, $-CF_3$, halogen, or $-C(O)W$, W may be $-OR_{12}$, $R_{12}$ being hydrogen allyl, $C_1-C_6$ alkyl, unsubstituted or mono- substituted phenyl, unsubstituted or mono-substituted phenyl $(C_1-C_3)$ alkyl, $(C_1-C_6)$ alkoxy $(C_2-C_4)$ alkyl, or $C_1-C_6$ haloalkyl, and $R_{14}$ is hydrogen or $C_1-C_6$ alkyl; or $R_4$ may be the group, $-C(O)Y$, Y being hydrogen, $C_1-C_6$ alkyl, $C_1-C_6$ alkoxy, unsubstituted, mono- or di-substituted phenyl, unsubstituted, mono- or di-substituted phenoxy, $R_5$ and $R_6$ may each be selected from the group consisting of hydrogen, $C_1-C_6$ alkyl, $C_5-C_7$ cycloalkyl, phenyl, mono- and di-substituted phenyl, or $R_5$ and $R_6$ together with the nitrogen atom may form an substituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, each of the aforedescribed phenyl, naphthyl, phenoxy and heterocyclic substituents being selected from the group consisting of hydroxy, amino, $C_1$–$C_6$ monoalkylamino, $C_1$–$C_6$ dialkylamino, i.e., di-($C_1$–$C_6$ alkyl)amino, piperidino, morpholino, pyrryl, indolinyl, pyrrolidyl, trimethylsilyloxy, $C_1$–$C_6$ alkyl, $C_1$–$C_6$ haloalkyl, $C_1$–$C_6$ alkoxy, mono($C_1$–$C_6$) alkoxy-($C_1$–$C_4$) alkyl, acryloxy, methacryloxy and halogen, each of the aforedescribed halogen or (halo) groups being fluoro or chloro.

Preferably $R_1$ is selected from the group consisting of —$SR_7$, —$OR_4$, —$N(R_5)R_6$, —$C(R_7)_2OH$, halogen, $C_1$–$C_4$ alkyl or the $C_3$–$C_6$ cycloalkyl, the mono-, di- and tri-substituted aryl group phenyl and naphthyl, the unsubstituted, mono- and di-substituted heterocyclic aromatic groups pyridyl, pyrrolyl, and indolyl; wherein $R_7$ is $C_1$–$C_4$ alkyl or the mono-, di- or tri-substituted aryl groups phenyl and naphthyl, $R_4$ is hydrogen, $C_1$–$C_6$ alkyl, or the group, —$C(O)Y$, wherein Y is hydrogen or $C_1$–$C_6$ alkyl; $R_5$ and $R_6$ are each selected from the group consisting of hydrogen, $C_1$–$C_6$ alkyl and phenyl, or $R_5$ and $R_6$ together with the nitrogen atom form an unsubstituted, mono-substituted or di-substituted heterocyclic ring selected from the group consisting of 1-indolinyl, morpholino, piperidino and 1-pyrrolidyl, each of the aforedescribed aryl (phenyl and naphthyl)and heterocyclic substituents being selected from the group consisting of hydroxy, amino, $C_1$–$C_4$ monoalkylamino, $C_1$–$C_4$ dialkylamino, piperidino, morpholino, pyrryl, indolinyl, pyrrolidyl, $C_1$–$C_4$ alkyl, $C_1$–$C_4$ haloalkyl, $C_1$–$C_4$ alkoxy, mono($C_1$–$C_4$)alkoxy $C_1$–$C_4$)alkyl and halogen, each of the aforedescribed halogen or (halo) groups being fluoro or chloro.

More preferably, $R_1$ is selected from the group consisting of —$SR_7$, —$OR_4$, —$N(R_5)R_6$, —$C(R_7)_2OH$, halogen, $C_1$–$C_2$ alkyl, the mono-, di- and tri- substituted aryl groups phenyl and naphthyl, the unsubstituted, mono- and di-substituted heterocyclic aromatic groups pyridyl and pyrrolyl; wherein $R_7$ is $C_1$–$C_4$ alkyl or phenyl, $R_4$ is hydrogen, $C_1$–$C_4$ alkyl or the group, —$C(O)Y$, wherein Y is $C_1$–$C_4$ alkyl; $R_5$ and $R_6$ are each selected from the group consisting of hydrogen or $C_1$–$C_4$ alkyl, or $R_5$ and $R_6$ together with the nitrogen atom form an unsubstituted, mono-substituted or di-substituted heterocyclic ring selected from the group consisting of 1-indolinyl, morpholino and piperidino, each of the aryl (phenyl and naphthyl) and heterocyclic substituents being selected from the group consisting of hydroxy, amino, $C_1$–$C_3$ monoalkylamino, $C_1$–$C_3$ dialkylamino, piperidino, morpholino, pyrryl, indolinyl pyrrolidyl, $C_1$–$C_3$ alkyl, $C_1$–$C_3$ haloalkyl, $C_1$–$C_3$ alkoxy, mono($C_1$–$C_3$)alkoxy ($C_1$–$C_4$)alkyl and halogen, each of the aforedescribed halogen or (halo) groups being fluoro or chloro. Most preferably, $R_1$ is n-methylpyrrol-2-yl, dimethoxyphenyl, phenylthio, chloro, methyl or diphenylmethylol.

$R_2$ in graphic formula I may be the group, —OR, $R_4$, $R_4$ being the same $R_4$ as defined in the description for $R_1$. Most preferably, $R_2$ is acetoxy, methoxy or hydroxy.

In graphic formula I, each $R_3$ may be selected from the group consisting of $C_1$–$C_6$ alkyl, $C_1$–$C_6$ alkoxy, halogen, unsubstituted and mono-substituted phenyl and unsubstituted and mono-substituted phenoxy. The aforesaid phenyl and phenoxy substituents may be selected from the group consisting of $C_1$–$C_6$ alkyl, $C_1$–$C_6$ alkoxy and halogen, each of the aforedescribed halogen groups being fluoro or chloro, and n may be selected from the integers 0, 1, 2, and 3.

Preferably, each $R_3$ is selected from the group consisting of $C_1$–$C_4$ alkyl, $C_1$–$C_4$ alkoxy, unsubstituted and mono-substituted phenyl and unsubstituted and mono-substituted phenoxy. The phenyl and phenoxy substituents being selected from the group consisting of $C_1$–$C_4$ alkyl, $C_1$–$C_4$ alkoxy and halogen, the halogen groups being fluoro or chloro and n is selected from the integers 0, 1 and 2.

More preferably, $R_3$ is selected from the group consisting of $C_1$–$C_2$ alkyl, $C_1$–$C_2$ alkoxy, unsubstituted and mono-substituted phenyl. The aforesaid phenyl substituents are selected from the group consisting of $C_1$–$C_3$ alkyl, $C_1$–$C_3$ alkoxy and halogen, each of the aforedescribed halogen being fluoro or chloro, and n is selected from the integers 0, 1 and 2. Most preferably, $R_3$ is methoxy or methyl, and n is 0 or 1.

In graphic formula I, B and B' may each be selected from the group consisting of: (i) the unsubstituted, mono-, di- and tri-substituted aryl groups phenyl and naphthyl; (ii) the unsubstituted, mono- and di-substituted heterocyclic aromatic groups pyridyl, furanyl, benzofuranyl, thienyl, benzothienyl, dibenzothienyl, dibenzofuranyl and carbazolyl, the phenyl, naphthyl and heterocyclic substituents being selected from the group consisting of hydroxy, amino, $C_1$–$C_6$ monoalkylamino, $C_1$–$C_6$ dialkylamino, i.e., di-($C_1$–$C_6$) alkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen, each of the halogen or (halo) substituents being fluoro or chloro; (iii) the groups represented by the following graphic formulae II A and II B:

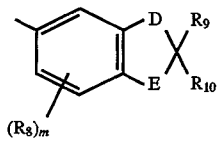

II A

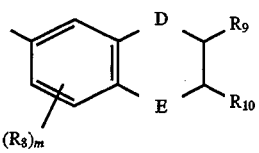

II B wherein D may be carbon or oxygen and E may be oxygen or substituted nitrogen, provided that when E is substituted nitrogen, D is carbon, said nitrogen substituent being selected from the group consisting of hydrogen, $C_1$–$C_6$ alkyl and $C_2$–$C_6$ acyl; each $R_8$ may be $C_1$–$C_6$ alkyl, $C_1$–$C_6$ alkoxy, hydroxy or halogen, wherein the halogen may be chloro or fluoro; $R_9$ and $R_{10}$ may each be hydrogen or $C_1$–$C_6$ alkyl; and m may be the integer 0, 1, or 2; (iv) $C_1$–$C_6$ alkyl, $C_1$–$C_6$ haloalkyl, $C_1$–$C_6$ alkoxy($C_1$–$C_4$)alkyl, $C_3$–$C_6$ cycloalkyl mono($C_1$–$C_6$)alkoxy($C_3$–$C_6$)cycloalkyl, mono($C_1$–$C_6$) alkyl-($C_3$–$C_6$) cycloalkyl, and halo($C_3$–$C_6$)cycloalkyl, said halo groups being fluoro or chloro; and (v) the group represented by the following graphic formula II C:

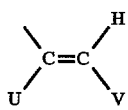

II C wherein U may be hydrogen or $C_1$–$C_4$ alkyl, and V may be selected from the unsubstituted, mono- and di-substituted members of the group consisting of naphthyl, phenyl, furanyl and thienyl, wherein the substituents for each member of said group are $C_1$–$C_4$ alkyl, $C_1$–$C_4$ alkoxy, fluoro, or chloro; or (vi) B and B' taken together may form an unsubstituted, mono-or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene, cyclododecylidene, saturated $C_7$–$C_{12}$ spiro-bicyclic hydrocarbon rings, e.g., bycyclo[2.2.1]heptylidene, i.e., norbornylidene, 1,7,7-trimethyl bicyclo[2.2.1]-heptylidene, i.e., bornylidene, bicyclo[3.2.1]octylidene, bicyclo[3.3.1]nonan-9-ylidene, bicyclo[4.3.2]undecane, and saturated $C_7$–$C_{12}$ spiro-tricyclic hydrocarbon rings, e.g., tricyclo[2.2.1.0$^{2,6}$]heptylidene, tricyclo[5.3.1.1$^{2,6}$]dodecyl-idene, and tricyclo [3.3.1.1$^{3,7}$]decylidene, i.e., adamantylidene, wherein the fluoren-9-ylidene substituents may be selected from the group consisting of $C_1$–$C_4$ alkyl, $C_1$–$C_4$ alkoxy, fluoro and chloro.

Preferably, B and B' are each selected from the group consisting of: (i) unsubstituted, mono-, di- and tri-substituted phenyl; (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, each of the phenyl and heterocyclic substituents being selected from the group consisting of morpholino, piperidino, $C_1$–$C_4$ alkyl, $C_1$–$C_4$ alkoxy and halogen, the halogen being fluoro or chloro; (iii) the groups represented by the graphic formula II A, wherein D is carbon and E is oxygen; each $R_8$ is $C_1$–$C_4$ alkyl, $C_1$–$C_4$ alkoxy, hydroxy or halogen, the halogen being chloro or fluoro; $R_9$ and $R_{10}$ are each hydrogen or $C_1$–$C_4$ alkyl; and m is the integer 0, 1 or 2; (iv) $C_1$–$C_4$ alkyl, $C_1$–$C_6$ alkoxy($C_1$–$C_4$)alkyl and $C_3$–$C_6$ cycloalkyl; and (v) the group represented by graphic formula II C, wherein U is hydrogen or methyl, and V is phenyl or mono-substituted phenyl, the phenyl substituent being $C_1$–$C_4$ alkyl, $C_1$–$C_4$ alkoxy or fluoro; or (vi) B and B' taken together form an unsubstituted or mono-substituted fluoren-9-ylidene, or a member selected from the group consisting of saturated $C_3$–$C_8$ spiro-monocyclic hydrocarbon rings, saturated $C_7$–$C_{10}$ spiro-bicyclic hydrocarbon rings and saturated $C_7$–$C_{10}$ spiro-tricyclic hydrocarbon rings.

More preferably, B and B' are each selected from the group consisting of: (i) unsubstituted, mono- and di-substituted phenyl; (ii) the unsubstituted, mono- and di-substituted heterocyclic aromatic groups pyridyl, benzofuran-2-yl, benzothien-2-yl, dibenzothienyl and dibenzofuranyl, each of the phenyl and heterocyclic substituents being selected from the group consisting of morpholino, piperidino, $C_1$–$C_2$ alkyl and $C_1$–$C_2$ alkoxy; and (iii) the groups represented by graphic formula II A, wherein D is carbon and E is oxygen; each $R_8$ is $C_1$–$C_2$ alkyl, $C_1$–$C_2$ alkoxy, or fluoro; $R_9$ and $R_{10}$ are each hydrogen or $C_1$–$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene. Most preferably, B and B' are each phenyl, methoxy substituted phenyl, morpholino substituted phenyl, dibenzofuran-2-yl, 2,3-dihydrobenzofuran-5-yl, or B and B' taken together form adamantylidene.

Compounds represented by graphic formula I may be prepared by the following steps. Benzophenones represented by graphic formula V and VA are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts. Acylation of 1,2,3,4-Tetrahydroquinoline and Related Nitrogen Heterocycles: Effect on NH Protective Groups and Ring Size" by Ishihara, Yugi et al, *J. Chem. Soc., Perkin Trans.* 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

REACTION A

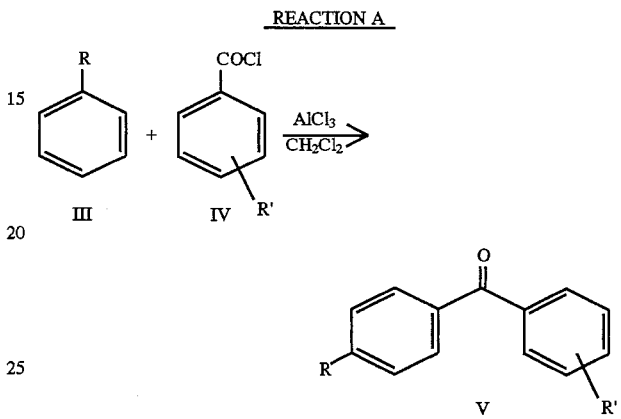

In Reaction B, the substituted or unsubstituted ketone represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared for example via reaction of an acyl halide with a substituted or unsubstituted benzene, naphthalene, or heteroaromatic compound. Propargyl alcohols having B or B' groups represented by graphic formula II C may be prepared by the methods described in U.S. Pat. No. 5,274,132, column 2, lines 40 to 68.

REACTION B

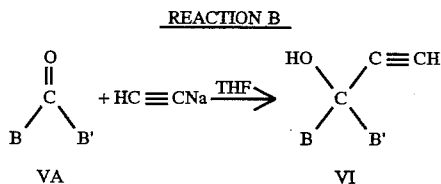

Compounds represented by graphic formula VII in Reaction C may either be purchased or prepared by addition or substitution reactions of quinones, which are described in "*The Chemistry of Quinonoid Compounds*", S. Patai, Wiley, 1974, Part 2, Chapter 17 (The Addition and Substitution Chemistry of Quinone); Katsuhira Yoshida, et. al., *Bull. Chem. Soc. Jpn*, 61, 1988, page 4335–4340; Katsuhira Yoshida, et. al., *Chemistry Express*, Vol. 5, No. 10, 1990, page 749–752; George W. Kabalka, *J. Organomet. Chem.*, 33, 1971, page C25–C28; Henk Pluim and Hans Wynberg, *J. Org. Chem.*, 45, 1980, page 2498–2502; Katsuhira Yoshida, et. al., *J. Chem. Soc., Perkin Trans. I*, 1994, page 2521–2523; Toshio Itahara, *J, Chem. Soc., Chem. Commun.*, 1981, page 859–860; Shmuel Bittner and Dorit Lempert, *Synthesis*, September 1994, page 917–919; and Katsuhira Yoshida, et. al., *Chem. Soc., Perkin Trans. I*, 1992, page 2713–2715.

The 2-substituted-1,4-dihydroxy naphthalenes may be prepared as described in Reactions C, D, and E. In Reaction C, the 2-substituted-1,4-naphthoquinone, represented by graphic formula VII, is reacted with zinc powder and acetic acid, to form a 2-substituted 1,4-dihydroxynaphthalene, represented by graphic formula VII A. This reaction is described further in *J. Chem. Soc. Perkin Trans. I*, 1994, page 2521–2523.

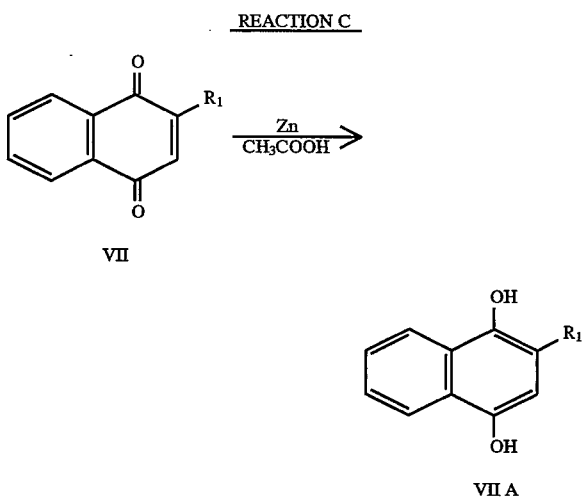

In Reaction D, 2-chloro-3-morpholino-1,4-naphthoquinone, which is commercially available and is represented by graphic formula VIII, is reacted with lithium aluminum hydride (LAH) in a suitable solvent such as anhydrous tetrahydrofuran (THF), to form 2-chloro-1,4-dihydroxy naphthalene, which is represented by graphic formula IX.

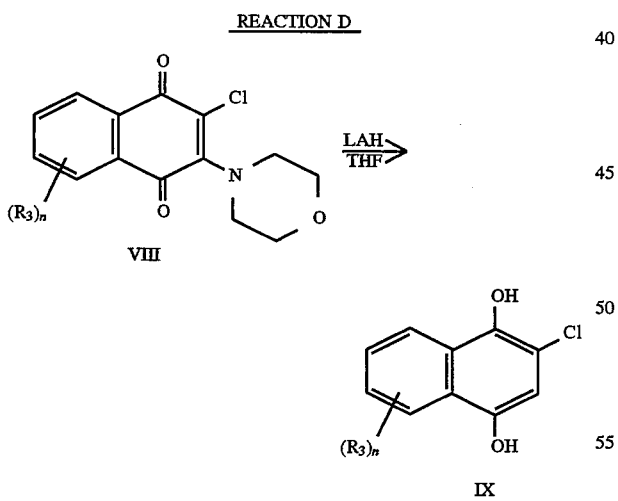

In reaction E, a substituted or unsubstituted 1,4-naphthoquinone, represented by graphic formula X, is reacted with a substituted or unsubstituted thiophenol, represented by graphic formula XI, in the presence of catalytic amount of 50 weight percent sulfuric acid in a suitable solvent such as acetic acid, to form the corresponding 2-phenylthio-1,4-dihydroxynaphthalene, represented by graphic formula XII.

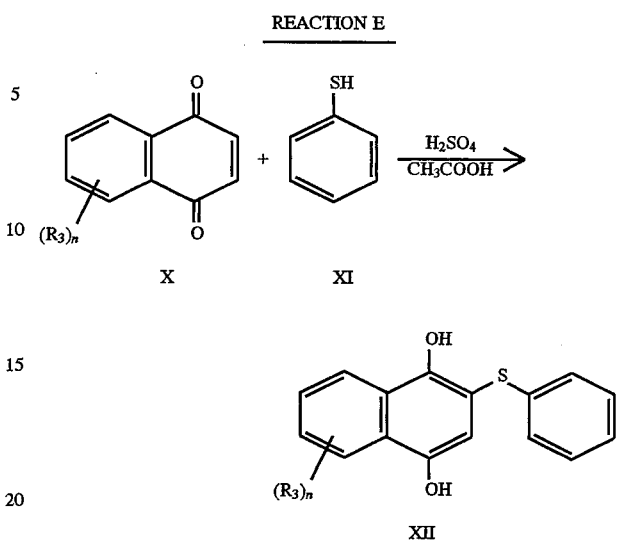

In Reaction F, the propargyl alcohol represented by graphic formula VI is coupled with the naphthols VII A, IX, or XII, or in more general terms with the naphthol represented by graphic formula VII B in the presence of a catalytic amount of para-toluenesulfonic acid (p-TsOH) in a suitable solvent such as toluene to form naphthopyrans represented by graphic formula XIII.

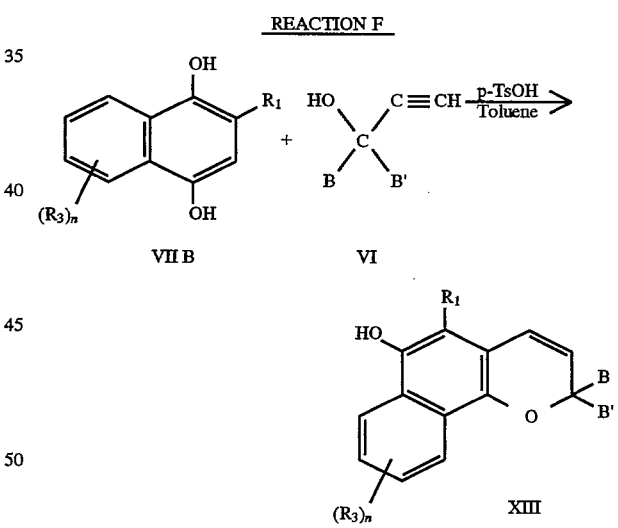

The $R_1$ substituent in formula XIII may be further modified as shown in Reaction G. For example, when $R_1$ is an ester and $R_2$ is —OH, the $R_1$ substituent can be converted to a variety of different groups by reacting such a compound, as represented by graphic formula XIV, with organometallics, such as Grignard reagents. For example, Compound XIV may be reacted with phenyl magnesium chloride [PhMgCl] (or other Grignard reagents) in a suitable solvent such as anhydrous tetrahydrofuran to form compounds represented by graphic formula XV, in which $R_1$ is a diphenylmethylol substituent.

REACTION G

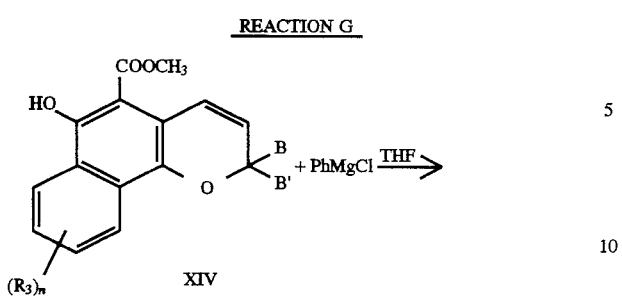

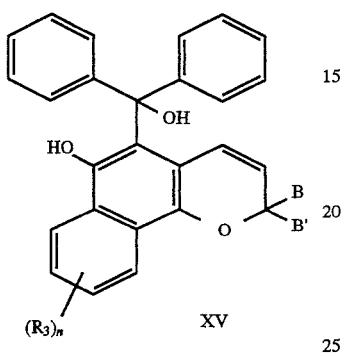

As shown in Reaction H, the 6-hydroxy substituent of compounds represented by graphic formula XIII can be converted to a variety of different groups by reaction with acylating or alkylating agents. For example, the compound represented by graphic formula XIII may be reacted with methyl iodide (or other alkylating agent) in the presence of anhydrous potassium carbonate in a suitable solvent such as anhydrous acetone to form compounds represented by graphic formula XVI, in which $R_2$ is a methoxy substitutent. Alkylating reactions are further described in "Organic Synthesis", Vol. 31, pages 90–93, John Wiley & Sons, Inc., New York, N.Y. Alternatively, Compound XIII may be reacted with acetyl chloride (or other acylating agent) in the presence of triethylamine ($NEt_3$) in an appropriate solvent, such as methylene chloride, to form compounds represented by the graphic formula XVII, in which $R_2$ is an acetoxy (AcO) substitutent. Acylating reactions are further described in "Organic Synthesis," Vol. 32, pages 72–77, John Wiley & Sons, Inc., New York, N.Y.

REACTION H

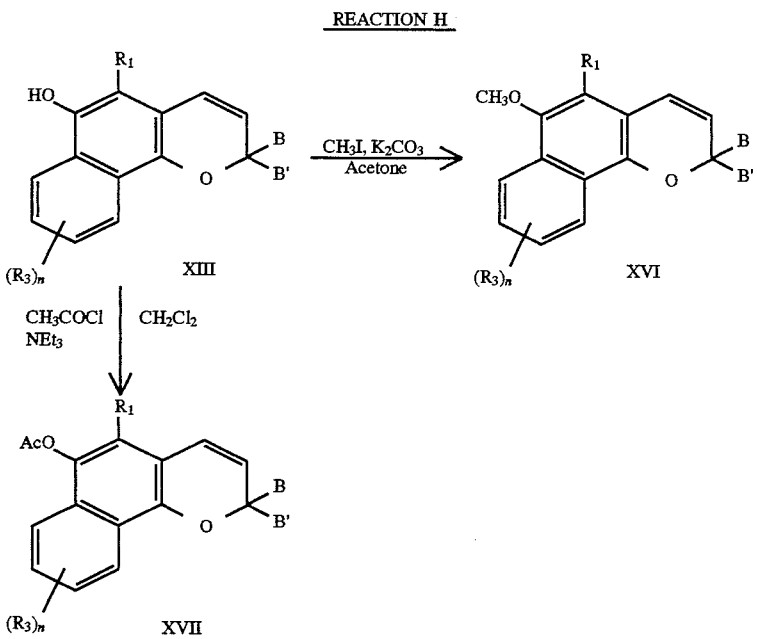

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to red/purple.

Examples of contemplated naphthopyrans within the scope of the invention are the following:

(a) 2,2-bis(4-methoxyphenyl)-5-(N-methylpyrrol-2-yl)-6-acetoxy-2H-naphtho[1,2-b]pyran;

(b) 2,2-bis(4-methoxyphenyl)-5-(2,4-dimethoxyphenyl)-6-acetoxy-2H-naphtho[1,2-b]pyran;

(c) 2,2-bis(4-methoxyphenyl)-5-phenylthio-6-hydroxy-2H-naphtho[1,2-b]pyran;

(d) 2,2-bis(4-methoxyphenyl)-5-phenylthio-6-acetoxy-2H-naphtho[1,2-b]pyran;

(e) 2,2-bis(4-methoxyphenyl)-5-chloro-6-acetoxy-2H-naphtho[1,2-b]pyran;

(f) 2,2-bis(4-methoxyphenyl)-5-methyl-6-acetoxy-2H-naphtho[1,2-b]pyran;

(g) 2,2'-spiroadamantylene-5-phenylthio-6-hydroxy-2H-naphtho[1,2-b]pyran;

(h) 2,2'-spiroadamantylene-5-phenylthio-6-acetoxy-2H-naphtho[1,2-b]pyran;

(i) 2,2'-spiroadamantylene-5-methyl-6-methoxy-2H-naphtho[1,2-b]pyran;

(j) 2,2-bis(4-methoxyphenyl)-5-diphenylmethylol-6-hydroxy-2H-naphtho[1,2-b]pyran; and (k) 2,2-bis(4-methoxyphenyl)-5-diphenylmethylol-6-methoxy-2H-naphtho[1,2-b]pyran.

It is contemplated that the organic photochromic naphthopyrans of graphic formula I be used in combination with other appropriate complementary organic photochromic materials so that together they produce a near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

The novel naphthopyran compounds of the present invention, such as those heretofore described, may be used alone or in combination with complementary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which compounds or mixtures of compounds color when activated to an appropriate hue.

A first group of complementary organic photochromic substances contemplated for use with the organic photochromic naphthopyrans of the present invention are those having an activated absorption maximum within the visible range of greater than 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668; spiro(indoline) naphthoxazines having certain substituents on the 8' and 9' positions of the naphthoxazine portion of the molecule are described in U.S. Pat. No. 5,405,958; spiro(indoline) pyridobenzoxazines are described in U.S. Pat. No. 4,637, 698; spiro(benzindoline)-pyridobenzoxazines and spiro (benzindoline)naphthoxazines are described in U.S. Pat. No. 4,931,219; spiro(benzindoline)-naphthopyrans are described in Japanese Patent Publication 62/195383; spiro(indoline) benzoxazines are described in U.S. Pat. No. 4,816,584; spiro(indoline)benzopyrans, spiro(indoline)-naphthopyrans, and spiro(indoline)quinopyrans are described, for example, in U.S. Pat. No. 4,880,667; and benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of complementary organic photochromic substances contemplated for use with the organic photochromic naphthopyrans of the present invention are those having at least one absorption maximum within the visible range of between about 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat Nos. 3,567,605; 4,826,977; and 5,066,818. Other examples of complementary benzopyrans and naphthopyrans that may be used with the naphthopyrans of the present invention include: those having a spiro adamantane group at the position alpha to the oxygen atom of the pyran ring, which are described in U.S. Pat. No. 4,826,977; 2H-naphtho-[1,2-b]pyran compounds having certain substitutents at the number 5 and 6 carbon atoms of the naphtho portion of the naphthopyran and at the 2 position of the pyran which are the subject of co-pending U.S. patent application Ser. No. 08/164,187, filed Dec. 9, 1993; 3H-naphtho[2,1-b]pyrans having at least one ortho-substituted phenyl substituent at the 3-position of the pyran ring which are described in U.S. Pat. No. 5,066,818; 3H-naphtho[2,1-b]pyran compounds having certain substituents at the number 8 carbon atom and certain substituents at the number 7 or 9 carbon atom, all substituents being on the naphtho portion of the naphthopyran, which are the subject of co-pending U.S. patent application Ser. No. 08/080,246, filed Jun. 21, 1993; 3H-naphtho[2,1-b]pyrans substituted at the 3 position of the pyran ring with (i) an aryl substituent and (ii) a phenyl substituent having a 5- or 6-member heterocyclic ring fused at the number 3 and 4 carbon atoms of the phenyl substituent are described in U.S. Pat. No. 5,384,077; diaryl-3H-naphtho [2,1-b]pyran compounds having a substituted or unsubstituted, 5 or 6 member heterocyclic ring fused to the g, i, or l side of the naphthopyran which are the subject of co-pending U.S. patent application Ser. No. 08/225,022 filed Apr. 8, 1994; naphthopyran compounds substituted at the number 8 carbon atom on the naphtho portion of the naphthopyran ring, with for example, a methoxy group which are the subject of U.S. Pat. No. 5,238,931; naphthopyran compounds, examples of which are 3-aryl-3-arylalkenyl naphtopyrans, which are described in U.S. Pat. No. 5,274,132; and naphtho[2,1-b]pyrans substituted at the number five carbon atom with, for example, an acetoxy group, which are the subject of U.S. Pat. No. 5,244,602.

A third group of complementary organic photochromic substances contemplated for use with the organic photochromic naphthopyrans of the present invention are those having an absorption maximum within the visible range of between about 400 to about 500 nanometers and another absorption maximum within the visible range of between about 500 to about 700 to nanometers. These materials typically exhibit color(s) ranging from yellow to purple and yellow/brown to purple/gray when exposed to ultraviolet light in an appropriate solvent or matrix. Examples of these compounds include certain substituted 2H-phenanthro[4,3-b]pyrans; substituted 3H-phenanthro[1,2-b]pyrans; and benzopyran compounds, such as those having substituents at the 2-position of the pyran ring and a substituted or unsubstituted heterocyclic ring, such as a benzothieno or benzofurano ring fused to the benz portion of the benzopyran. Such later described compounds are the subject of co-pending U.S. patent application Nos. 08/286,039 filed Aug. 4, 1994 and U.S. Pat. No. 5,411,679.

Photochromic articles of the present invention may contain one photochromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as a second group photochromic compound) may be used also in combination with the organic photochromic substances of the first complementary group of photochromic compounds described herein, i.e., those that color to colors blue, blueish-green, or blueish-purple or with other organic photochromic substances in the aforesaid second group of photochromic compounds. Either members of the first or second group of photochromic compounds or mixtures of such compounds may be combined with or used in conjunction with the third group described herein that exhibit colors ranging from yellow to purple and yellow/brown to purple/gray.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied. When mixtures of the aforedescribed organic photochromic complementary groups are used, the weight ratio of such materials, i.e., (first to second), (second to third), and (naphthopyran of the present invention to other second group compounds) will vary from about 1:3 to about 3:1, e.g., between about 0.75:1 and about 2:1. The combination of the first, second, and third described organic photochromic complementary groups may have a weight ratio that will vary from about 1:3:1 to 3:1:3.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance if the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720, 356. Finally, appropriate protective coating(s) may be applied to the surface of the host material. These may be abrasion resistant coatings and/or coatings that serve as oxygen barriers. Such coatings are known in the art.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multi-functional, acrylate and/or methacrylate monomers, polyacrylates, polymethacrylates, poly($C_1$–$C_{12}$ alkyl methacrylates) such as poly(methyl methacrylate), polyoxy (alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66.

The present invention is more particularly described in the following examples which are intended as illustrative only, since numerous modifications and variations therein will be apparent to those skilled in the art.

EXAMPLE 1

Step 1

1,4-Naphthoquinone (5 grams (g), 0.031 mole), N-methylpyrrole (20 g, 0.248 mole) and copper acetate (6.2 g, 0.031 mole) were added to a reaction flask containing 50 milliliters (ml) of acetic acid under nitrogen and stirred. After approximately 3 hours, the mixture was filtered and zinc powder (8 g) was added to the filtrate and stirred under nitrogen for 30 minutes at room temperature. The resulting mixture was filtered and the residue was washed with 25 ml of chloroform. The filtrates were combined and 100 ml of water was added. The resulting mixture was extracted with three 25 ml portions of chloroform. The organic extracts were combined, washed with distilled water, and dried over magnesium sulfate. The solvent, chloroform was removed under vacuum to yield a crude product containing 2-(N-methylpyrrol-2-yl)-1,4-dihydroxynaphthalene, which was not purified further but used directly in Step 3.

Step 2

4,4'-Dimethoxybenzophenone (65 g, 0.27 mole) was dissolved in a reaction flask containing 200 ml of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After stirring 16 hours at room temperature under a nitrogen atmosphere, the contents of the reaction flask were added to a 5 weight percent aqueous hydrochloric acid and ice mixture. The resulting mixture was extracted with diethyl ether, washed, and dried over anhydrous sodium sulfate. The solvents, diethyl ether and tetrahydrofuran, were removed under vacuum to yield an oily product. The resulting product was induced to crystallize from a diethyl ether:hexane mixture. The recovered product (about 60 g) had a melting point of 83°–84° C. A nuclear magnetic resonance (NMR) spectrum showed the product to have a structure consistent with 1,1-bis(4-methoxyphenyl)-2-propyn-1-ol.

Step 3

2-(N-methylpyrrol-2-yl)-1,4-dihydroxynaphthalene (2 g, 0.0083 mole) from Step 1 and 1,1-bis(4-methoxyphenyl)-2-propyn-1-ol (2.25 gm, 0.0083 mole) from Step 2 were added to a reaction flask containing 50 ml of toluene and stirred at room temperature. A catalytic amount of p-toluenesulfonic acid (about 100 mg) was added and stirred for 4 hours under a nitrogen atmosphere. Triethylamine (2 ml) was added and the reaction mixture was stirred for 5 minutes. Acetyl chloride (2 ml) was slowly added and the reaction mixture was stirred for 1 hour. Distilled water (50 ml) was added to the reaction flask and the reaction mixture was stirred for 30 minutes. The organic layer was separated, washed and dried over anhydrous sodium sulfate. Evaporation of solvent resulted in an oily product which was purified using a silica gel column and a 1:1 mixture of chloroform:hexane as the eluant. The photochromic fractions were combined and the eluant was removed under vacuum. The resulting product was induced to crystallize from diethyl ether. The recovered product (about 500 mg) had a melting point of 185°–186° C. A nuclear magnetic resonance (NMR) spectrum showed the product to have a structure consistent with 2,2-bis(4-methoxyphenyl)-5-(N-methylpyrrol-2-yl)-6-acetoxy-2H-naphtho[1,2-b]pyran.

EXAMPLE 2

Step 1

1,4-Naphthoquinone (5 g, 0.031 mole) and 1,3-dimethoxybenzene (5 g, 0.036 mole) were added to a reaction flask containing 100 ml of acetic acid. Sulfuric acid (3.0 ml of a 50% weight percent aqueous solution) was added to the reaction mixture and the mixture was refluxed for 1 hour. The reaction mixture was cooled to room temperature and poured into water. The resulting precipitate was collected by filtration, washed with water, and dried. The resulting product containing 2-(2,4-dimethoxyphenyl)-1,4-dihydroxynaphthalene was not purified but used directly in the next step.

Step 2

The procedure of Step 3 of example 1 was followed except that 2-(2,4-dimethoxyphenyl)-1,4-dihydroxynaphthalene (3.0 g) prepared in step 1 was used in place of 2-(N-methylpyrrol-2-yl)-1,4-dihydroxynaphthalene. The recovered product, 1.2 g, had a melting point of 234°–235° C. A nuclear magnetic resonance (NMR) spectrum showed the desired product to have a structure consistent with 2,2-bis(4-methoxyphenyl)-5-(2,4-dimethoxyphenyl)-6-acetoxy-2H-naphtho[1,2-b]pyran.

EXAMPLE 3

Step 1

The procedure of Step 1 of Example 2 was followed except that thiophenol was used in place of 1,3-dimethoxybenzene to produce 2-phenylthio-1,4-dihydroxynaphthalene.

Step 2

2-Phenylthio-1,4-dihydroxynaphthalene (2 g) from Step 1 and 1,1-bis(4-methoxyphenyl)-2-propyn-1-1-ol (2.25 g) from Step 2 of Example 1 were added to a reaction flask containing 70 ml of toluene and stirred at room temperature. A catalytic amount of p-toluenesulfonic acid (about 100 mg) was added and stirred for 4 hours under a nitrogen atmosphere. Afterwards, the reaction mixture was poured into 50 ml of 10 weight percent aqueous sodium hydroxide solution. The organic layer was separated, washed and dried over anhydrous sodium sulfate. Evaporation of solvent resulted in an oily product which was purified using a silica gel column and a 1:1 mixture of chloroform:hexane as the eluant. The photochromic fractions were combined and the eluant was removed under vacuum. The resulting product was induced to crystallize from diethyl ether. The recovered product (2.5 g) had a melting point of 152°–154° C. A nuclear magnetic resonance (NMR) spectrum showed the product to have a structure consistent with 2,2-bis(4-methoxyphenyl)-5-phenylthio-6-hydroxy-2H-naphtho[1,2-b]pyran.

EXAMPLE 4

Step 1

2,2-Bis(4-methoxyphenyl)-5-phenylthio-6-hydroxy-[2H]-naphtho[1,2-b]pyran (2 g), prepared as described in Example 3, and triethylamine (2 g) were added to a reaction flask containing 50 ml of methylene chloride and stirred. Acetyl chloride (2 g) was added to the reaction flask and the reaction mixture was stirred for 1 hour. Afterwards, the organic layer was separated, washed, and dried over anhydrous sodium sulfate. Evaporation of solvent resulted in an oily residue that was crystallized from diethyl ether. The solid was suction filtered, washed with hexane, and air dried. The resulting product had a melting point of 125°–126° C. A nuclear magnetic resonance (NMR) spectrum showed the product to have a structure consistent with 2,2-bis(4-methoxyphenyl)-5-phenylthio-6-acetoxy-2H-naphtho[1,2-b]pyran.

EXAMPLE 5

Step 1

2-Chloro-3-morpholino-1,4-naphthoquinone (5 g, 0.012 mole) was added to a reaction flask containing 50 ml of tetrahydrofuran under nitrogen and stirred. Lithium aluminum hydride (2 g) was added slowly and stirred for 2 hours at room temperature. Hydrochloric acid (100 ml of a 10 weight percent solution) was added and the resulting mixture was extracted with three 25 ml portions of diethyl ether. The organic extracts were combined, washed with distilled water, and dried over magnesium sulfate. Evaporation of solvent resulted in an oily residue that was crystallized from diethyl ether. The solid was suction filtered, washed with hexane, and air dried. The resulting solid product (2.5 g) was used directly in the next step. A nuclear magnetic resonance (NMR) spectrum showed this product to have a structure consistent with 2-chloro-1,4-dihydroxynaphthalene Step 2

The procedure of Step 3 of Example 1 was followed except that 2-chloro-1,4-dihydroxynaphthalene (3.0 g) prepared in Step 1 was used in place of 2-(N-methylpyrrol-2-yl)-1,4-dihydroxynaphthalene. The recovered product, 2.5 g, had a melting point of 168°–169° C. A nuclear magnetic resonance (NMR) spectrum showed the isolated product to have a structure consistent with 2,2-bis(4-methoxyphenyl)-5-chloro-6-acetoxy-2H-naphtho[1,2-b]pyran.

EXAMPLE 6

Step 1

2-Methyl-1,4-naphthoquinone (5 g, 0.029 mole) was added to a reaction flask containing 50 ml of acetic acid under nitrogen. Zinc powder (8 g) was added to the flask and stirred under nitrogen for 30 minutes at room temperature. The mixture was filtered and residue was washed with 25 ml of chloroform. The filtrates were combined and 100 ml of water was added. The resulting mixture was extracted with three 25 ml portions of chloroform. The organic extracts were combined, washed with distilled water, and dried over magnesium sulfate. Evaporation of solvent resulted in an oily residue that was crystallized from diethyl ether. The solid was suction filtered, washed with hexane and air dried. The resulting solid product (4 g) was used directly in the next step. A nuclear magnetic resonance (NMR) spectrum showed the isolated product to have a structure consistent with 2-methyl-1,4-dihydroxynaphthalene.

Step 2

The procedure of Step 3 of Example 1 was followed except that 2-methyl-1,4-dihydroxynaphthalene (3.0 g) from Step 1 was used in place of 2-(N-methylpyrrol-2-yl)-1,4-dihydroxynaphthalene. The recovered product, 4 g, had a melting point of 158°–159° C. A nuclear magnetic resonance (NMR) spectrum showed the isolated product to have a structure consistent with 2,2-bis(4-methoxyphenyl)-5-methyl-6-acetoxy-2H-naphtho[1,2-b]pyran.

EXAMPLE 7

The procedure of Step 2 of Example 1 was followed except that adamantanone was used in place of 4,4'-dimethoxybenzophenone to produce 2-ethinyl-2-hydroxyadamantane. The procedure of Step 2 of Example 3 was followed except that 2-ethinyl-2-hydroxyadamantane was used in place of 1,1-bis(4-methoxyphenyl)-2-propyn-1-ol to produce the desired product. A nuclear magnetic resonance (NMR) spectrum showed the isolated product to have a structure consistent with 2,2'-spiroadamantylene-5-phenylthio-6-hydroxy-2H-naphtho[1,2-b]pyran.

EXAMPLE 8

The procedure of Step 1 of Example 4 was followed except that 2,2'-spiroadamantylene-5-phenylthio-6-hydroxy-2H-naphtho [1,2-b]pyran was used in place of 2,2-bis(4-methoxyphenyl)-5-phenylthio-6-hydroxy-2H-naphtho [1,2-b]pyran to produce the desired product. A nuclear magnetic resonance (NMR) spectrum showed the desired product to have a structure consistent with 2,2'-spiroadamantylene-5-phenylthio-6-acetoxy-2H-naphtho[1,2-b]pyran.

EXAMPLE 9

Step 1

The procedure of Step 2 of Example 3 was followed except that 2-ethinyl-2-hydroxyadamantane was used in place of 1,1-bis(4-methoxyphenyl)-2-propyn-1-ol and 2-methyl-1,4-dihydroxynaphthalene was used in place of 2-phenylthio-1,4-dihydroxynaphthalene to produce 2,2'-spiroadamantylene-5-methyl-6-hydroxy-2H-naphtho[1,2-b]pyran.

Step 2

2,2'-Spiroadamantylene-5-methyl-6-hydroxy-[2H]-naphtho [1,2-]pyran(2 g) from Step 1, anhydrous potassium carbonate (2 g), and methyl iodide (2 g) were added to a reaction flask containing 40 ml of anhydrous acetone, stirred and refluxed under an argon atmosphere. Afterwards, the acetone was removed under vacuum and 25 ml each of water and methylene chloride were added to the reaction mixture. The organic layer was separated, washed with distilled water, and dried over magnesium sulfate. Evaporation of solvent resulted in an oily residue that was crystallized from diethyl ether. The solid was suction filtered, washed with hexane, and air dried. The recovered product, 1.8 g, had a melting point of 136°–137° C. A nuclear magnetic resonance (NMR) spectrum showed the isolated product to have a structure consistent with 2,2'-spiroadamantylene-5-methyl-6-methoxy-2H-naphtho[1,2-b]pyran.

EXAMPLE 10

Step 1

The procedure of Step 2 of Example 3 was followed except that methyl-1,4-dihydroxynaphthoate was used in place of 2-phenylthio-1,4-dihydroxynaphthalene. The recovered product, 4 g, had a melting point of 160° C. A nuclear magnetic resonance (NMR) spectrum showed the isolated product to have a structure consistent with 2,2-bis(4-methoxyphenyl)-5-methoxycarbonyl-6-hydroxy-2H-naphtho[1,2-b]pyran.

Step 2

2,2-Bis(4-methoxyphenyl)-5-methoxycarbonyl-6-hydroxy-2H-naphtho[1,2-b]pyran(2 g) from Step 1 was added to a reaction flask containing 30 ml of anhydrous tetrahydrofuran and stirred. Phenyl magnesium chloride (10 ml of a 3 molar solution purchased from Aldrich) was slowly added to the reaction mixture and stirred at room temperature for an hour. Hydrochloric acid (50 ml of a 10 weight percent solution) was added. The resulting mixture was extracted with three 25 ml portions of diethyl ether. The organic extracts were combined, washed with distilled water, and dried over magnesium sulfate. Evaporation of solvent resulted in an oily residue that was crystallized from diethyl ether. The solid was suction filtered, washed with hexane, and air dried. The recovered product, 2.2 g, had a melting point of 132°–134° C. A nuclear magnetic resonance (NMR) spectrum showed the desired product to have a structure consistent with 2,2-bis (4-methoxyphenyl)-5-diphenylmethylol-6-hydroxy-2H-naphtho[1,2-b]pyran.

EXAMPLE 11

Step 1

The procedure of Step 2 of Example 9 was followed except that 2,2-bis(4-methoxyphenyl)-5-diphenylmethylol-6-hydroxy-2H-naphtho[1,2-b]pyran(2.0 g) was used in place of 2,2'-spiroadamantylene-5-methyl-6-hydroxy-[2H]-naphtho[1,2-b]pyran. The recovered product, 1.5 g, had a melting point of 221°–223° C. A nuclear magnetic resonance (NMR) spectrum showed the desired product to have a structure consistent with 2,2-bis(4-methoxyphenyl)-5-diphenylmethylol-6-methoxy-[2H]-naphtho[1,2-b]pyran.

EXAMPLE 12

Part A

Testing was done with the photochromic naphthopyrans of the Examples incorporated into polymeric samples by the following method. The quantity of naphthopyran calculated to yield a 1.5 time $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis (2-methyl propionitrile) (AIBN). The naphthopyran was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C. for at least 2 hours before the end of the curing cycle. After the mold was opened, the polymer sheet was cut using a diamond blade saw into 2 inch (5.1 centimeters) test squares.

Part B

The photochromic test squares prepared in Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle normal to the square. After passing through the square, the light from the tungsten lamp was directed through a photopic filter attached to a detector. The photopic filter passes wavelengths such that the detector mimics the response of the human eye. The output signals from the detector(s) were processed by a radiometer.

Change in optical density ($\Delta$OD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state; and calculating the change in optical density according to the formula $\Delta$ OD=log(100/%Ta) where %Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 20 minutes for the examples in Table 1. The lambda max reported in Table 1 is the wavelength in the visible spectrum at which the maximum absorption of the activated (colored) form of the photochromic compound in a diethylene glycol bis(allyl carbonate) composition occurs. The Bleach Rate (T ½) is the time interval in seconds for the absorbance of the activated form of the naphthopyran in the test squares to reach one half the highest absorbance at room temperature (75° F., 23.9° C.) after removal of the source of activating light. Results for the Compounds of the Examples are tabulated in Table 1.

TABLE 1

| EXAMPLE COMPOUNDS | LAMBDA MAX (VISIBLE) | $\Delta$OD/MIN SENSITIVITY | $\Delta$OD@ SATURATION | Bleach (T1/2) |
|---|---|---|---|---|
| 1 | 513 nm | 0.16 | 0.25 | 74 |
| 2 | 511 nm | 0.15 | 0.55 | 248 |
| 3 | 516 nm | 0.34 | 1.76 | >600 |
| 4 | 516 nm | 0.22 | 0.23 | 42 |
| 5 | 462 nm | 0.08 | 0.07 | 54 |
| 6 | 506 nm | 0.14 | 0.37 | 120 |
| 7 | 462 nm | 0.15 | 0.47 | 185 |
| 8 | 459 nm | 0.10 | 0.04 | 68 |
| 9 | 462 nm | 0.12 | 0.17 | 153 |
| 10 | 482 nm | 0.05 | 0.32 | >800 |
| 11 | 467 nm | 0.10 | 0.19 | 85 |

The results of Table 1 show that a range of values for bleach rate, $\Delta$OD at saturation, and sensitivity are obtained for the Example Compounds 1 through 11 of the present invention depending on the nature of substituents $R_1$, $R_2$, $R_3$, and B and B'.

Although the present invention has been described with reference to the specific details of particular embodiments thereof, it is not intended that such details be regarded as limitations upon the scope of the invention except as and to the extent that they are included in the accompanying claims.

I claim:

1. A naphthopyran compound represented by the following graphic formula:

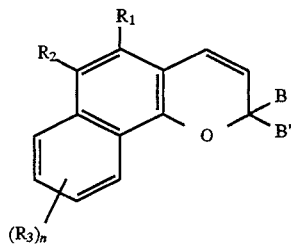

wherein, (a) $R_1$ is selected from the group consisting of, —$SR_7$, —$OR_4$, —CH(COO$R_7$)$_2$, —CH$_2$COO$R_7$, —N($R_5$)$R_6$, —N($R_7$)C(O)$R_7$, —C($R_7$)$_2$OH, —CN, —CF$_3$, halogen, $C_1$–$C_6$ alkyl, $C_3$–$C_7$ cycloalkyl, the mono-, di- and tri-substituted aryl groups phenyl and naphthyl, unsubstituted and mono-substituted phenyl($C_1$–$C_3$)alkyl, unsubstituted and mono-substituted naphthyl($C_1$–$C_3$) alkyl, ($C_1$–$C_6$)alkoxy($C_2$–$C_4$)alkyl, the unsubstituted, mono- and di-substituted heterocyclic aromatic groups pyridyl, pyrrolyl, indolyl, furanyl, benzofuranyl, thienyl and benzothienyl; wherein $R_7$ is $C_1$–$C_6$ alkyl, or the mono-, di- or tri-substituted aryl groups phenyl and naphthyl, $R_4$ is hydrogen, $C_1$–$C_6$ alky, the mono- or di-substituted aryl groups phenyl and naphthyl, unsubstituted or mono-substituted phenyl($C_1$–$C_3$)alkyl, unsubstituted or mono-substituted naphthyl($C_1$–$C_3$) alkyl, ($C_1$–$C_6$)alkoxy($C_2$–$C_4$)alkyl, $C_3$–$C_7$ cycloalkyl, mono($C_1$–$C_4$)alkyl substituted C3–$C_7$ cycloalkyl, $C_1$–$C_6$ haloalkyl, allyl, the group, —CH($R_{14}$)X, wherein X is —CN, —CF$_3$, halogen, or —C(O)W, W being —O$R_{12}$, wherein $R_{12}$ is hydrogen, allyl, $C_1$–$C_6$ alkyl, unsubstituted or mono-substituted phenyl, unsubstituted or mono-substituted phenyl ($C_1$–$C_3$) alkyl, ($C_1$–$C_6$)alkoxy($C_2$–$C_4$)alkyl, or $C_1$–$C_6$ haloalkyl, and $R_{14}$ is hydrogen or $C_1$–$C_6$ alkyl; or $R_4$ is the group;

—C(O)Y, wherein Y is hydrogen, $C_1$–$C_6$ alkyl, $C_1$–$C_6$ alkoxy, unsubstituted, mono- or disubstituted phenyl, unsubstituted, mono- or di-substituted phenoxy, $R_5$ and $R_6$ are each selected from the group consisting of hydrogen, $C_1$–$C_6$ alkyl, $C_5$–$C_7$ cycloalkyl, phenyl, mono- or di-substituted phenyl, or $R_5$ and $R_6$ together with the nitrogen atom form an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, each of the said phenyl, phenoxy and heterocyclic substituents being selected from the group consisting of hydroxy, amino, $C_1$–$C_6$ monoalkylamino, $C_1$–$C_6$ dialkylamino, piperidino, morpholino, pyrryl, indolinyl, pyrrolidyl, trimethylsilyloxy, $C_1$–$C_6$ alkyl, $C_1$–$C_6$ haloalkyl, $C_1$–$C_6$ alkoxy, mono($C_1$–$C_6$)alkoxy ($C_1$–$C_4$)alkyl, acryloxy, methacryloxy and halogen, each of said halogen or (halo) groups being fluoro or chloro;

(b) $R_2$ is the group, —$OR_4$, $R_4$ being the same as defined in (a);

(c) each $R_3$ is selected from the group consisting of $C_1$–$C_6$ alkyl, $C_1$–$C_6$ alkoxy, halogen, unsubstituted and mono-substituted phenyl, unsubstituted and mono-substituted phenoxy, said phenyl and phenoxy substituents being selected from the group consisting of $C_1$–$C_6$ alkyl, $C_1$–$C_6$ alkoxy and halogen, each of said halogen groups being fluoro or chloro, and n is selected from the integers 0, 1, 2, and 3;

(d) B and B' are each selected from the group consisting of:

(i) the unsubstituted, mono-, di- and tri-substituted aryl groups phenyl and naphthyl, (ii) the unsubstituted, mono- and di-substituted heterocyclic aromatic groups pyridyl, furanyl, benzofuranyl, thienyl, benzothienyl, dibenzothienyl, dibenzofuranyl, and carbazolyl, said phenyl, naphthyl and heterocyclic substituents being selected from the group consisting of hydroxy, amino, $C_1$–$C_6$ monoalkylamino, $C_1$–$C_6$ dialkylamino, piperidino, morpholino, 1-indolinyl, pyrrolidyl, 1-imidazolidyl, 2-imidazolin-1-yl, 2-pyrazolidyl, pyrazolinyl, 1-piperazinyl, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen, each of said halogen or (halo) groups being fluoro or chloro;

(iii) the groups represented by the following graphic formulae:

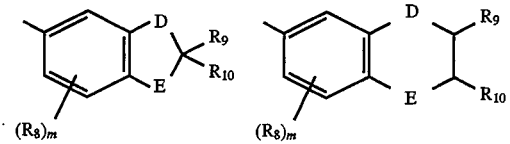

wherein D is carbon or oxygen and E is oxygen or substituted nitrogen, provided that when E is substituted nitrogen, D is carbon, said nitrogen substituent being selected from the group consisting of hydrogen, $C_1$–$C_6$ alkyl and $C_2$–$C_6$ acyl, each $R_8$ is $C_1$–$C_6$ alkyl, $C_1$–$C_6$ alkoxy, hydroxy or halogen, said halogen being chloro or fluoro; $R_9$ and $R_{10}$ are each hydrogen or $C_1$–$C_6$ alkyl; and m is the integer 0, 1, or 2;

(iv) $C_1$–$C_6$ alkyl, $C_1$–$C_6$ haloalkyl, $C_1$–$C_6$ alkoxy ($C_1$–$C_4$) alkyl, $C_3$–$C_6$ cycloalkyl, mono ($C_1$–$C_6$) alkoxy ($C_3$–$C_6$) cycloalkyl, mono ($C_1$–$C_6$) alkyl ($C_3$–$C_6$) cycloalkyl and halo($C_3$–$C_6$)cycloalkyl, said halo groups being fluoro or chloro; and (v) the group represented by the following graphic formula:

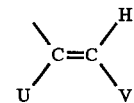

wherein U is hydrogen or $C_1$–$C_4$ alkyl, and V is selected from the group consisting of the unsubstituted, mono- and di-substituted members of the group consisting of naphthyl, phenyl, furanyl and thienyl, wherein the substituents for each member of said group are $C_1$–$C_4$ alkyl, $C_1$–$C_4$ alkoxy, fluoro, or chloro; or (vi) B and B' taken together form an unsubstituted, mono- or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, said fluoren-9-ylidene substituents being selected from the group consisting of $C_1$–$C_4$ alkyl, $C_1$–$C_4$ alkoxy, fluoro and chloro.

2. The naphthopyran of claim 1 wherein:

(a) $R_1$ is selected from the group consisting of —$SR_7$, —$OR_4$, —$N(R_5)R_6$, —$C(R_7)_2OH$, halogen, $C_1$–$C_4$ alkyl, $C_3$–$C_6$ cycloalkyl, the mono, di- and tri- substituted aryl groups, phenyl and naphthyl, the unsubstituted, mono- and di-substituted heterocyclic aromatic groups pyridyl, pyrrolyl and indolyl; wherein $R_7$ is $C_1$–$C_4$ alkyl or the mono-, di- or tri-substituted aryl groups phenyl and naphthyl, $R_4$ is hydrogen or $C_1$–$C_6$ alkyl, or the group, —C(O)Y, wherein Y is hydrogen or $C_1$–$C_6$ alkyl; $R_5$ and $R_6$ are each selected from the group consisting of hydrogen, $C_1$–$C_6$ alkyl and phenyl, or $R_5$ and $R_6$ together with the nitrogen atom form an unsubstituted, mono-substituted or di-substituted heterocyclic ring selected from the group consisting of 1-indolinyl, morpholino, piperidino and 1-pyrrolidyl, each of said phenyl, naphthyl and heterocyclic substituents being selected from the group consisting of hydroxy, amino, $C_1$–$C_4$ monoalkylamino, $C_1$–$C_4$ dialkylamino, piperidino, morpholino, pyrryl, indolinyl, pyrrolidyl, $C_1$–$C_4$ alkyl, $C_1$–$C_4$ haloalkyl, $C_1$–$C_4$ alkoxy, mono($C_1$–$C_4$)alkoxy($C_1$–$C_4$)alkyl and halogen, each of said halogen or (halo) groups being fluoro or chloro;

(b) $R_2$ is the group, —$OR_4$, $R_4$ being the same as defined in (a);

(c) each $R_3$ is selected from the group consisting of $C_1$–$C_4$ alkyl, $C_1$–$C_4$ alkoxy, unsubstituted and mono-substituted phenyl, and unsubstituted and mono-substituted phenoxy, said phenyl and phenoxy substituents being selected from the group consisting of $C_1$–$C_4$ alkyl, $C_1$–$C_4$ alkoxy, and halogen, said halogen being fluoro or chloro, and n is selected from the integers 0, 1 and 2; and (d) B and B' are each selected from the group consisting of:

(i) unsubstituted, mono-, di- and tri-substituted phenyl;

(ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, each of said phenyl and heterocyclic substituents being selected from the group consisting of morpholino, piperidino, $C_1$-$C_4$ alkyl, $C_1$-$C_4$ alkoxy and halogen, said halogen being fluoro or chloro;

(iii) the groups represented by the following graphic formula:

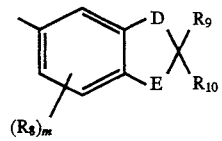

wherein D is carbon and E is oxygen; each $R_8$ is $C_1$-$C_4$ alkyl, $C_1$-$C_4$ alkoxy, hydroxy or halogen, said halogen being chloro or fluoro; $R_9$ and $R_{10}$ are each hydrogen or $C_1$-$C_4$ alkyl; and m is the integer 0, 1 or 2;

(iv) $C_1$-$C_4$ alkyl, $C_1$-$C_6$ alkoxy($C_1$-$C_4$)alkyl and $C_3$-$C_6$ cycloalkyl; and (v) the group represented by the following graphic formula:

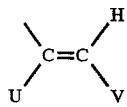

wherein U is hydrogen or methyl, and V is phenyl or mono-substituted phenyl, said phenyl substituent being $C_1$-$C_4$ alkyl, $C_1$-$C_4$ alkoxy or fluoro; or (vi) B and B' taken together form an unsubstituted or mono-substituted fluoren-9-ylidene, or a member selected from the group consisting of saturated $C_3$-$C_8$ spiro-monocyclic hydrocarbon rings, saturated $C_7$-$C_{10}$ spiro-bicyclic hydrocarbon rings and saturated $C_7$-$C_{10}$ spiro-tricyclic hydrocarbon rings.

3. The naphthopyran of claim 2 wherein:

(a) $R_1$ is selected from the group consisting of —$SR_7$, —$OR_4$, —$N(R_5)R_6$, —$C(R_7)_2OH$, halogen, $C_1$-$C_2$ alkyl, the mono-, di- and tri- substituted aryl groups phenyl and naphthyl, the unsubstituted, mono- and di-substituted heterocyclic aromatic groups pyridyl and pyrrolyl; wherein $R_7$ is $C_1$-$C_4$ alkyl or phenyl, $R_4$ is hydrogen, $C_1$-$C_4$ alkyl or the group, —C(O)Y, wherein Y is $C_1$-$C_4$ alkyl; $R_5$ and $R_6$ are each selected from the group consisting of hydrogen and $C_1$-$C_4$ alkyl, or $R_5$ and $R_6$ together with the nitrogen atom form an unsubstituted, mono-substituted or di-substituted heterocyclic ring selected from the group consisting of 1-indolinyl, morpholino and piperidino, each of said phenyl, naphthyl and heterocyclic substituents being selected from the group consisting of hydroxy, amino, $C_1$-$C_3$ monoalkylamino, $C_1$-$C_3$ dialkylamino, piperidino, morpholino, pyrryl, indolinyl, pyrrolidyl, $C_1$-$C_3$ alkyl, $C_1$-$C_3$ haloalkyl, $C_1$-$C_3$ alkoxy, mono ($C_1$-$C_3$)alkoxy($C_1$-$C_4$)alkyl and halogen, each of said halogen or (halo) groups being fluoro or chloro;

(b) $R_2$ is the group, —$OR_4$, $R_4$ being the same as defined in (a);

(c) $R_3$ is selected from the group consisting of $C_1$-$C_2$ alkyl, $C_1$-$C_2$ alkoxy, unsubstituted and mono-substituted phenyl, said phenyl substituents being selected from the group consisting of $C_1$-$C_3$ alkyl, $C_1$-$C_3$ alkoxy, and halogen, the halogen being fluoro or chloro, and n is selected from the integers 0, 1 and 2; and (d) B and B' are each selected from the group consisting of:

(i) unsubstituted, mono- and di-substituted phenyl;

(ii) the unsubstituted, mono- and di-substituted heterocyclic aromatic groups pyridyl, benzofuran-2-yl, benzothien-2-yl, dibenzothienyl and dibenzofuranyl, each of said phenyl and heterocyclic substituents being selected from the group consisting of morpholino, piperidino, $C_1$-$C_2$ alkyl and $C_1$-$C_2$ alkoxy; and (iii) the groups represented by the following graphic formula:

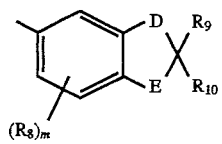

wherein D is carbon and E is oxygen; each $R_8$ is $C_1$-$C_2$ alkyl, $C_1$-$C_2$ alkoxy or fluoro; $R_9$ and $R_{10}$ are each hydrogen or $C_1$-$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene.

4. The naphthopyran of claim 3 wherein $R_1$ is n-methylpyrrol-2-yl, dimethoxyphenyl, phenylthio, chloro, methyl or diphenylmethylol; $R_2$ is acetoxy, methoxy or hydroxy; $R_3$ is methoxy or methyl, and n is 0 or 1; and B and B' are each phenyl, methoxy substituted phenyl, morpholino substituted phenyl, dibenzofuran-2-yl, or 2,3-dihydrobenzofuran-5-yl, or B and B' taken together form adamantylidene.

5. A naphthopyran compound selected from the group consisting of:

(a) 2,2-bis(4-methoxyphenyl)-5-(N-methylpyrrol-2-yl)-6-acetoxy-2H-naphtho[1,2-b]pyran;

(b) 2,2-bis(4-methoxyphenyl)-5-(2,4-dimethoxyphenyl)-6-acetoxy-2H-naphtho[1,2-b]pyran;

(c) 2,2-bis(4-methoxyphenyl)-5-phenylthio-6-hydroxy-2H-naphtho[1,2-b]pyran;

(d) 2,2-bis(4-methoxyphenyl)-5-phenylthio-6-acetoxy-2H-naphtho[1,2-b]pyran;

(e) 2,2-bis(4-methoxyphenyl)-5-chloro-6-acetoxy-2H-naphtho[1,2-b]pyran;

(f) 2,2-bis(4-methoxyphenyl)-5-methyl-6-acetoxy-2H-naphtho[1,2-b]pyran;

(g) 2,2'-spiroadamantylene-5-phenylthio-6-hydroxy-2H-naphtho[1,2-b]pyran;

(h) 2,2'-spiroadamantylene-5-phenylthio-6-acetoxy-2H-naphtho[1,2-b]pyran;

(i) 2,2'-spiroadamantylene-5-methyl-6-methoxy-2H-naphtho[1,2-b]pyran;

(j) 2,2-bis(4-methoxyphenyl)-5-diphenylmethylol-6-hydroxy-2H-naphtho[1,2-b]pyran; and (k) 2,2-bis(4-methoxyphenyl)-5-diphenylmethylol-6-methoxy-2H-naphtho[1,2-b]pyran.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance (s) is incorporated or applied.

12. The photochromic article of claim 11 wherein the article is a lens.

13. A photochromic article comprising a photochromic amount of the naphthopyran compound of claim 3 and a polymeric organic host material selected from the group consisting of poly(methyl methacrylate), poly(ethylene glycol his methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 4 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 15 wherein the organic photochromic compound (b) is selected from the group consisting of:
   (a) organic photochromic substances having at least one absorption maximum in the visible range of between 400 and less than 500 nanometers;
   (b) organic photochromic substances having an absorption maximum within the visible range of between about 400 and 500 nanometers and an absorption maximum within the visible range of between 500 and 700 nanometers; and
   (c) organic photochromic substances having an activated absorption maxima in the visible range of greater than 570 nanometers; and
   (d) mixtures of said organic photochromic substances.

18. The photochromic article of claim 17 wherein the organic photochromic compound (b) is an organic photochromic substances having an activated absorption maxima in the visible range of greater than 570 nanometers.

19. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

20. The photochromic article of claim 17 wherein the organic photochromic compound (b) is selected from the group consisting of spiro(indoline)naphthoxazines, spiro (indoline)-pyridobenzoxazines, spiro(benzindoline) pyridobenzoxazines, spiro(benzindoline)naphthoxazines, spiro(benzindoline)naphthopyrans, spiro(indoline) benzoxazines, spiro(indoline)benzopyrans, spiro(indoline) naphthopyrans, spiro(indoline)quinopyrans, spiro(indoline) pyrans, 3H-naphtho[2,1-b]pyrans, 2H-phenanthro[4,3-b] pyrans; 3H-phenanthro[1,2-b]pyrans; benzopyran compounds and mixtures of such photochromic substances.

* * * * *

UNITED STATES PATENT AND TRADEMARK OFFICE
CERTIFICATE OF CORRECTION

PATENT NO. : 5,658,501
DATED : August 19, 1997
INVENTOR(S) : Anil Kumar et al

It is certified that error appears in the above-indentified patent and that said Letters Patent is hereby corrected as shown below:

Column 3, line 53, should read, "$R_2$ in graphic formula I may be the group, $-OR_4$, $R_4$".

Signed and Sealed this

Twenty-first Day of September, 1999

*Attest:*

Q. TODD DICKINSON

*Attesting Officer*    *Acting Commissioner of Patents and Trademarks*